US 6,898,991 B2

(12) United States Patent
Geise et al.

(10) Patent No.: US 6,898,991 B2
(45) Date of Patent: May 31, 2005

(54) SAMPLER FOR DUST ON SURFACES

(75) Inventors: Ulrich Geise, Osterholz-Scharmbeck (DE); Gerhard Weiss, Weyhe (DE)

(73) Assignee: Bruker Daltonik GmbH, Bremen (DE)

( * ) Notice: Subject to any disclaimer, the term of this patent is extended or adjusted under 35 U.S.C. 154(b) by 86 days.

(21) Appl. No.: 10/283,020

(22) Filed: Oct. 29, 2002

(65) Prior Publication Data

US 2003/0096428 A1 May 22, 2003

(30) Foreign Application Priority Data

Oct. 30, 2001 (DE) ......................................... 101 53 084

(51) Int. Cl.$^7$ ................................................ G01N 1/14
(52) U.S. Cl. ................................................ 73/864.52
(58) Field of Search ........................ 73/864.51, 864.52, 73/863.23, 863.24, 863.21, 863.22, 864.71; 141/8

(56) References Cited

U.S. PATENT DOCUMENTS

| | | | |
|---|---|---|---|
| 3,026,730 A | | 3/1962 | Howarth et al. |
| 3,136,440 A | * | 6/1964 | Krug et al. ................. 215/247 |
| 3,362,141 A | * | 1/1968 | Royster, Jr. et al. ..... 73/863.23 |
| 3,494,351 A | | 2/1970 | Horn |
| 3,522,734 A | * | 8/1970 | Curby ....................... 73/863.21 |
| 3,706,305 A | | 12/1972 | Berger et al. |
| 3,748,905 A | * | 7/1973 | Fletcher et al. .......... 73/863.25 |
| 3,901,765 A | | 8/1975 | Mehl |
| 3,977,555 A | * | 8/1976 | Larson ....................... 215/247 |
| 4,066,067 A | | 1/1978 | Micheli |
| 4,154,229 A | * | 5/1979 | Nugent ........................ 600/577 |
| 4,197,610 A | * | 4/1980 | Schneider ..................... 15/383 |
| 4,281,066 A | | 7/1981 | Thran et al. |
| 4,301,936 A | * | 11/1981 | Percarpio .................... 215/247 |
| 4,303,069 A | * | 12/1981 | Cohen ........................ 604/201 |
| 4,499,930 A | * | 2/1985 | Walters .......................... 141/8 |
| 4,564,054 A | * | 1/1986 | Gustavsson ................. 141/329 |
| 4,652,429 A | | 3/1987 | Konrad |
| 4,660,423 A | * | 4/1987 | Armstrong et al. ....... 73/864.52 |
| 4,909,090 A | * | 3/1990 | McGown et al. ......... 73/864.33 |
| 4,925,627 A | * | 5/1990 | Johnson ........................ 422/99 |
| 4,980,297 A | | 12/1990 | Haynes et al. |
| 6,199,436 B1 | | 3/2001 | Morel et al. |
| 6,550,347 B2 | * | 4/2003 | Bradley ................... 73/863.21 |

FOREIGN PATENT DOCUMENTS

| | | |
|---|---|---|
| DE | 29 48 653 A1 | 6/1981 |
| EP | 0 469 427 A1 | 2/1992 |
| EP | 0 901 824 A2 | 3/1999 |

* cited by examiner

*Primary Examiner*—Charles Garber

(57) ABSTRACT

The invention relates to a collector which is able to take small samples of possibly hazardous dusts lying scattered on a surface. The invention consists of an evacuated sampling bottle closed with a septum, which is to be provided with a telescopic cap which has a contact plate shaped for removing the dust or liquid sample from a small surface by suction and a needle which can puncture the septum. The sample bottle can be filled with a small amount of liquid to take up the dust. When the sample bottle is held in the hand and the cap is pressed onto a surface which is coated with dust or liquid droplets, the needle punctures the septum and the vacuum sucks some of the dust or liquid droplets into the sample bottle.

10 Claims, 1 Drawing Sheet

SAMPLER FOR DUST ON SURFACES

FIELD OF THE INVENTION

The invention relates to a collector which is able to take small samples of possibly hazardous dusts lying scattered on a surface.

BACKGROUND OF THE INVENTION

Analysis of scattered dust or liquid droplets which may be highly poisonous or highly infectious requires a quick and simple method of sampling which reliably rules out any risk to the sampler. In particular, the sampling process should prevent the dust from being made airborne as the sample is collected.

The samples are used for chemical or biological identification using analytical systems which are not the subject of this description. One example is mass spectrometers which are capable of identifying dangerous chemicals or bacterial spores in dusts in a short time of only a few minutes even in a diluted state using pyrolyzing devices and the measurement of characteristic daughter ions of pyrolyzed substances. Another example of the analysis of infectious dusts is conventional incubation and cultivation methods. These, however, take longer to carry out.

Dust suction systems which deposit the dust in filters are known. However, removing the filters, their further processing and cleaning the dust suction unit are problematic, not least because of the risk to the person handling them. Similar difficulties and risks are associated with the known wiping techniques.

SUMMARY OF THE INVENTION

The invention makes use of commonly used sampling bottles with capacities such as 10 ml which are closed with a septum and evacuated by means of a small vacuum pump a few days, or preferably hours, before use. As the septum is punctured with a small hollow needle, air is sucked in at the other end of the needle together with the dust. A suitable holder for the needle can be shaped so that the dust or liquid droplets can be easily sampled from the surface.

The sampling bottles are connected with an inexpensive plastic device, for example, with a small, plane collection plate with tiny feet or pimples and a suction hole in the center, which passes into the small needle. The plastic device consists of two telescopic parts which can be pushed together under light pressure—a clip component for placing on the bottle and a needle component with a pimpled collection plate. The collection plate with the pimples can be placed on the surface coated with dust, the pimples producing a small gap between the collection plate and the surface on which the dust is lying. If the telescoping device is now pushed together with slight pressure, the needle, which is rigidly attached to the collection plate, punctures the septum and the vacuum sucks the dust or droplets of the liquid from the vicinity of the hole in the center of the collection plate. The samples are sucked into the collection bottle, where they can be taken up in a small amount of liquid such as water.

The device in this example, which is made from inexpensive plastic, can be easily pulled off the bottle and disposed of. The dust sample is securely enclosed in the collection bottle and can be taken to the location where the analysis is to be carried out. Since no dust is made airborne, the surface of the bottle usually remains clean. If there is a small amount of liquid in the sampling bottle, such as approximately 100 to 500 $\mu$l water, then the dust binds to the liquid as it impinges on the inner surface of the bottle, provided that the interior surface is moistened with the liquid. Shaking the bottle afterwards helps the liquid to bind the dust. The liquid containing the dust can be easily extracted by means of a syringe and processed in the usual way without any further risk of the dust dispersing in the air.

The collection plate of the plastic device can be approximately 10 to 20 mm in diameter and have three to six small pimples approximately 0.5 to 1 mm high. The pimples are placed on the surface coated with dust. The gap between the collection plate of the device and the dust-coated surface creates the ideal conditions for sucking the dust from a surface of around 5 to 10 mm diameter without making the dust in the surrounding area airborne.

DETAILED DESCRIPTION

If pre-evacuated bottles are not being used, a number of sample bottles is evacuated before starting the sampling procedure. For evacuation, the septum of the sampling bottle is punctured by a syringe needle which is connected to a small vacuum pump. This may be a battery powered membrane pump or even, if necessary, a water-jet pump or a small hand pump.

Sample bottles which are sealed with a screw cap fitted with a so-called septum are commercially available. The septum normally consists of a soft silicone rubber usually coated with a thin layer of PTFE (polytetrafluoroethylene). These sample bottles, which are normally used in chromatography, can be filled and emptied by puncturing with injection needles without the puncture leaving a hole. The closure re-seals, vacuum tight, when the needle is withdrawn. The sample bottles are numbered clearly so that sampling can be easily recorded.

Evacuated bottles hold the vacuum for a period of time lasting days; if sterile bottles are stored in suitable vacuum packaging, no evacuation at all is necessary. Otherwise, it is expedient not to carry out the evacuation until a few hours before sampling.

Dangerous substances are best bound in the sample bottles by a small quantity of liquid, preferably water. The water is placed in the bottles before they are evacuated. Immediately before use, the bottle can be shaken in order to moisten the interior surface with liquid. After the dust has been sampled, the bottle is shaken again in order to bind the liquid with the dust.

Figure 1:
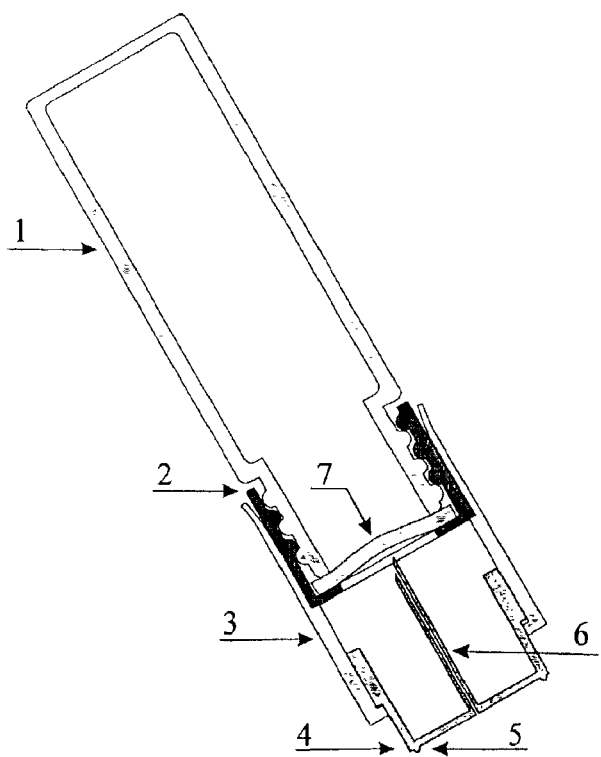
FIG. 1 shows a cross section of the dust-collection device with sample bottle (1), screw cap (2), septum (7), clip (3) for the cap and needle component (4) of the plastic device with pimples (5) and needle (6).
Figure 2:
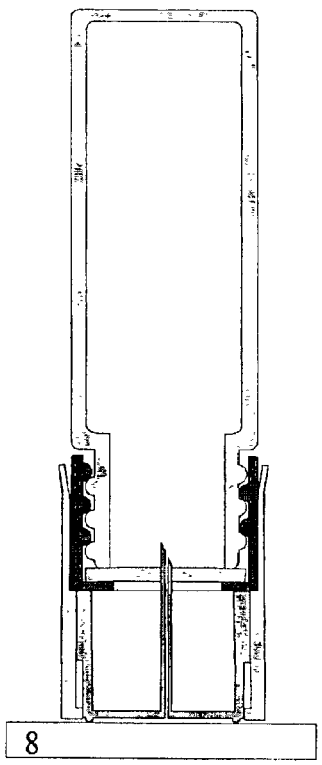
FIG. 2 shows the dust collection device after pressing onto a surface (8) previously coated with dust where the needle (6) has punctured the septum (7).

A preferred embodiment of the bottle (1) with the plastic device in place is shown in FIG. 1. The device, which is made from inexpensive plastic, is in two parts. A clip (3) can be placed on the bottle cap (2). In this clip (3), which is attached to the bottle sufficiently firmly, there is a second, easily movable needle component (4) incorporating the collection plate with pimples (5), the needle (6) and a hole in the center. The movable needle component (4) can be pushed into the firmly fixed clip component (3), whereby the needle (6) punctures the septum (7).

If the collection surface with the pimples (5) is placed on the surface (8) coated with dust, the pimples produce a small gap between the collection surface and the surface (8) coated with dust. The sampling plate assists the sampling process which follows but prevents the dust beyond the collection site from being made airborne. If the layer of dust on the surface is too thin, a strip of paper can be used to push it together carefully. If the bottle is now pushed in the direction of the surface coated with dust, the needle (6) punctures the septum (7) and the dust in the gap is transported by the air stream into the sample bottle (1).

If there is liquid inside the sample bottle, then the liquid is atomized to form a mist as the dust is collected. The mist binds a large portion of the dust and is deposited again relatively quickly. On shaking the bottle, the remaining dust (and mist) binds to the liquid. The dust can now be extracted using a syringe without any risk of dispersion and then taken for analysis.

The dust collection device can be transported in a small, sterilizable case along with a battery-powered pump and other accessories such as protective gloves and a face mask.

What is claimed is:

1. Sampling device for dust lying on surfaces, the device comprising:
    (a) an evacuated sampling vessel having a membrane which can be punctured; and
    (b) a movable needle fixed to the sampling vessel that can puncture the membrane with a first end and take up the dust sample at a second end simultaneously, the second end of the needle opening into a collection plate with pimples which can be pressed onto the surface coated with dust such that the pimples keep a small distance between the surface and the needle opening.

2. Sampling device according to claim 1 wherein the sampling vessel is a sampling bottle closed with a screw cap with a septum forming the membrane which can be punctured.

3. Sampling device according to claim 2 wherein there is a two-component telescopic device on the closure cap of the sample bottle with a clip component and a movable needle component placed on it, where the movement of the needle component has the effect of causing one end of the needle to puncture the septum.

4. Sampling device according to claim 1 wherein the membrane or the septum has such a thickness and elasticity that the puncture closes vacuum-tight again when the needle is withdrawn.

5. Sampling device according to claim 1, further comprising a small amount of liquid in the sample vessel to which the dust binds when drawn into the vessel.

6. Method according to claim 5, wherein the liquid comprises water.

7. Method for the sampling of dusts deposited on surfaces, the method comprising:
    providing an evacuated sampling bottle having a membrane that can be punctured and a movable needle connected to the sampling vessel, wherein a first end of the needle resides adjacent to the membrane, and a second end of the needle for taking up the dust sample opens out into a pimpled collection plate which can be placed on a surface coated with dust; and
    pressing the sample collection device against the surface coated with dust to cause the septum to be punctured by the first end of the needle and the dust sample to be sucked into the sampling bottle through the needle.

8. Method according to claim 7 wherein the sampling vessel is evacuated by means of a suction pump through a needle which is inserted by puncture before the sample is collected.

9. Method according to claim 7, further comprising providing a small amount of liquid in the sample vessel to which the dust binds when drawn into the vessel.

10. Method according to claim 9, wherein the liquid comprises water.

* * * * *